United States Patent
Ji et al.

(10) Patent No.: US 11,878,963 B2
(45) Date of Patent: Jan. 23, 2024

(54) SEMI SYNTHETIC METHOD FOR DIHYDROQUERCETIN

(71) Applicant: HEFEI LIFEON PHARMACEUTICAL CO., LTD., Anhui (CN)

(72) Inventors: Junqiu Ji, Anhui (CN); Xiaochang Li, Anhui (CN); Qiao Li, Anhui (CN); Jun Chen, Anhui (CN); Bing Li, Anhui (CN); Ruru Liu, Anhui (CN); Xiaohong Zhao, Anhui (CN)

(73) Assignee: HEFEI LIFEON PHARMACEUTICAL CO., LTD., Anhui (CN)

( * ) Notice: Subject to any disclaimer, the term of this patent is extended or adjusted under 35 U.S.C. 154(b) by 0 days.

(21) Appl. No.: 18/008,099

(22) PCT Filed: May 7, 2022

(86) PCT No.: PCT/CN2022/091501
§ 371 (c)(1),
(2) Date: Dec. 2, 2022

(87) PCT Pub. No.: WO2020/237690
PCT Pub. Date: Nov. 17, 2022

(65) Prior Publication Data
US 2023/0192640 A1 Jun. 22, 2023

(30) Foreign Application Priority Data
May 10, 2021 (CN) .......................... 202110508758.6

(51) Int. Cl.
*C07D 311/32* (2006.01)
*C07D 311/40* (2006.01)

(52) U.S. Cl.
CPC .......... *C07D 311/32* (2013.01); *C07D 311/40* (2013.01); *C07B 2200/13* (2013.01)

(58) Field of Classification Search
CPC .......................... C07D 311/32; C07D 311/40
See application file for complete search history.

(56) References Cited

U.S. PATENT DOCUMENTS

| 2,744,920 A | 5/1956 | Kurth |
| 2016/0362401 A1 | 12/2016 | Venkateswara et al. |

FOREIGN PATENT DOCUMENTS

| CN | 101863869 A | 10/2010 |
| CN | 101993429 A | 3/2011 |
| CN | 103044379 A | 4/2013 |
| CN | 103570663 A | 2/2014 |
| CN | 104024229 A | 9/2014 |
| CN | 104024429 A | 9/2014 |
| CN | 104387357 A | 3/2015 |
| CN | 105283442 A | 1/2016 |
| CN | 105348063 A | 2/2016 |
| CN | 106103419 A | 11/2016 |
| CN | 107880081 A | 4/2018 |
| CN | 110467592 A | 11/2019 |
| CN | 112375043 A | 2/2021 |
| CN | 113185485 A | 7/2021 |
| CN | 113214210 A | 8/2021 |
| EP | 2143435 A | 1/2010 |
| EP | 2850069 A1 | 3/2015 |
| WO | WO 2013/172693 A1 | 11/2013 |

OTHER PUBLICATIONS

Sambher, Shikha et al., ARKIVOC (2009), (10), 140-144.*
International Search Report and Written Opinion for International App. No. PCT/CN2022/091501 dated Jul. 27, 2022.
Yu et al., Review on the Properties of Thiourea Dioxide and Reduction of Organic Compounds with It. Fine Chem. Intermediates. Jun. 30, 2014;44(3). 5 pages.
U.S. Appl. 18,008,044, filed Dec. 2, 2022, Ji et al.
PCT/CN2022/091501, Jul. 27, 2022, International Search Report and Written Opinion.

\* cited by examiner

*Primary Examiner* — Valerie Rodriguez-Garcia
(74) *Attorney, Agent, or Firm* — Wolf, Greenfield & Sacks, P.C.

(57) ABSTRACT

The present disclosure provides a semi-synthetic method of dihydroquercetin, belonging to the field of synthesis of organic drugs. The semi-synthetic method includes the following steps: adding quercetin dihydrate to solvent water adjusted to be alkaline with an alkalizing reagent, heating and stirring to dissolve the mixture, and then adding thiourea dioxide under the protection of an inert gas to perform a reduction reaction, to obtain an endpoint reduction reaction solution; diluting the endpoint reduction reaction solution with water and cooling the resultant, and then acidizing, aging, and filtering the resultant to obtain a filtrate and a filter cake; extracting, washing, drying, concentrating, and repeatedly crystallizing the filtrate to obtain dihydroquercetin; and recycling the filter cake after being washed.

20 Claims, 5 Drawing Sheets

SEMI SYNTHETIC METHOD FOR DIHYDROQUERCETIN

CROSS-REFERENCE TO RELATED APPLICATIONS

The present disclosure is a National Stage filing under 35 U.S.C. 371 of International PCT Application No. PCT/CN2022/091501, filed May 7, 2022, which claims the priority to the Chinese patent application with the filing No. CN 202110508758.6 filed with the Chinese Patent Office on May 10, 2021 and entitled "Semi-synthetic Method of Dihydroquercetin", the contents of which are incorporated herein by reference in their entirety.

TECHNICAL FIELD

The present disclosure relates to the field of synthesis of organic drugs, and in particular, to a semi-synthetic method of dihydroquercetin.

BACKGROUND ART

Dihydroquercetin, having a chemical name of 3,3',4',5,7-pentahydroxy-flavanonol, is also called as taxifolin, and has a structural formula as follows:

Formula (I)

Compared with quercetin, dihydroquercetin has better dissolving behavior in ethanol and water, and thus has broader and more practical biological activity than quercetin, such as: oxidation resistance, or affecting fat metabolism by regulating enzyme activity, or inhibiting growth of malignant lymphocytes and leukemia cells, or functioning to inhibit bacteria (Staphylococcus aureus, Escherichia coli, Shigella dysenteriae, and Typhoid bacillus, etc.), and also inhibiting viral enzymes. Therefore, the dihydroquercetin has a wide promotion and application prospect in fields such as health care products, functional foods, medicines, cosmetics, and industry and agriculture.

Up to now, preparation methods of dihydroquercetin mainly include two major categories, i.e. a phytochemistry method and a chemical synthetic method. The dihydroquercetin has a low content in plants, separation and purification processes after extraction are complex, and this method is destructive to plant resources (such as roots of Pseudotsuga Menziesii) under condition of large-scale production. The chemical synthetic method can be divided into a full-synthetic method and a semi-synthetic method. Although the former has readily available raw materials and is easy to achieve large-scale production, the synthesis steps are relatively long, and there are problems such as toxicity of raw materials, reagents, and solvents, and different degrees of "three-waste" contamination, therefore, the full-synthetic method lacks prospects for industrial application. Moreover, unless asymmetric synthetic method is employed, the full-synthetic method can hardly render a target product which is consistent or nearly consistent with natural dihydroquercetin in absolute configuration.

SUMMARY

The present disclosure provides a semi-synthetic method of dihydroquercetin, including the following steps:
adding quercetin dihydrate to reaction solvent water adjusted to be alkaline with an alkalizing reagent, heating and stirring to dissolve the mixture, and then adding thiourea dioxide under the protection of an inert gas to perform a reduction reaction, to obtain an endpoint reduction reaction solution;
diluting the endpoint reduction reaction solution with addition of water and cooling the resultant, and then acidizing, aging, and filtering the resultant to obtain a filtrate and a filter cake; and
extracting, washing, drying and concentrating the filtrate to obtain a concentrated crude product of dihydroquercetin, and then repeatedly crystallizing (recrystallizing) the concentrated crude product of dihydroquercetin to obtain the dihydroquercetin.

In some optional embodiments of the present disclosure, a mass ratio of the quercetin dihydrate to the reaction solvent water is 1:120-220. In some optional embodiments of the present disclosure, the mass ratio of the quercetin dihydrate to the reaction solvent water is 1:140-200. In some typical embodiments, the mass ratio of the quercetin dihydrate to the reaction solvent water is 1:160-180. In some embodiments of the present disclosure, the alkalizing reagent includes at least one of sodium carbonate, potassium carbonate, and calcium carbonate. In some typical embodiments, the alkalizing reagent is at least one of sodium carbonate and potassium carbonate. In some embodiments of the present disclosure, a molar ratio of the quercetin dihydrate to the alkalizing reagent is 1:3.5-6.5. In some typical embodiments, the molar ratio of the quercetin dihydrate to the alkalizing reagent is 1:4.5-5.5.

In some optional embodiments of the present disclosure, a molar ratio of the quercetin dihydrate to the thiourea dioxide is 1:2.5-7.5. In some typical embodiments, the molar ratio of the quercetin dihydrate to the thiourea dioxide is 1:3.0-7.0. In some typical embodiments, the molar ratio of the quercetin dihydrate to the thiourea dioxide is 1:3.5-6.5.

In some optional embodiments of the present disclosure, a reaction temperature of the reduction reaction is 60-100° C. In some typical embodiments, the reaction temperature of the reduction reaction is 70-90° C. In some optional embodiments of the present disclosure, reaction time of the reduction reaction is 60-120 min. In some typical embodiments, the reaction time of the reduction reaction is 70-110 min.

In some optional embodiments of the present disclosure, the acidizing process refers to acidification of a diluted reduction reaction solution with a dilute acid. In some optional embodiments of the present disclosure, the dilute acid includes at least one of dilute hydrochloric acid, dilute sulfuric acid, and dilute acetic acid. In some typical embodiments, the dilute acid is dilute hydrochloric acid. In some embodiments, molar concentration of the dilute hydrochloric acid is 1.0-4.0 mol/L. In some typical embodiments, the molar concentration of the dilute hydrochloric acid is 2.0-3.0 mol/L. In some embodiments, a pH value of an acidification endpoint is 0.5-3.5. In some typical embodiments, the pH value of the acidification endpoint is 2.0-3.0.

In some optional embodiments of the present disclosure, the resulting filter cake is recycled after being washed with a dilute alcohol solution.

In some embodiments, the dilute alcohol solution includes dilute methanol or dilute ethanol. In some embodiments, a concentration of alcohol in the dilute alcohol solution is 10%-80%. In some typical embodiments, the concentration of the alcohol in the dilute alcohol solution is 20%-60%. In some embodiments, the washing lasts for 10-30 min. In some typical embodiments, the washing lasts for 15-25 min. In some embodiments, temperature of the washing is room temperature to 60° C. In some typical embodiments, the temperature of the washing is room temperature to 40° C. In some optional embodiments of the present disclosure, an extraction solvent used in the extraction is a hydrophobic organic solvent. In some embodiments, the hydrophobic organic solvent includes at least one of an aliphatic ether, an alicyclic ether, an aliphatic ester, and a hydrophobic aliphatic ketone. In some embodiments, the hydrophobic organic solvent includes at least one of isopropyl ether, tert-butyl ether, ethyl acetate, isopropyl acetate, and methyl isobutyl ketone.

In some optional embodiments of the present disclosure, the process of repeated crystallization includes: subjecting a concentrated crude product to primary crystallization to obtain a primary crystallization product; and crystallizing the primary crystallization product once again to obtain a secondary crystallization product. In some embodiments, the solvent used for repeated crystallization includes a mixed solvent of lower aliphatic alcohol and water. In some typical embodiments, the lower aliphatic alcohol includes at least one of methanol, ethanol, and isopropanol.

In some optional embodiments of the present disclosure, concentration of the lower aliphatic alcohol contained in the alcohol-water mixed solvent for repeated crystallization is 20%-80%. In some typical embodiments, the concentration of the lower aliphatic alcohol contained in the alcohol-water mixed solvent for repeated crystallization is 30%-70%. In some typical embodiments, the concentration of the lower aliphatic alcohol contained in the alcohol-water mixed solvent for repeated crystallization is 40%-60%. In some optional embodiments of the present disclosure, in the primary crystallization, a material-liquid ratio of the concentrated crude product to the solvent for repeated crystallization is 1:3.0-10.0. In some typical embodiments, the material-liquid ratio of the concentrated crude product to the solvent for repeated crystallization is 1:5.0-8.0.

In some embodiments, in the secondary crystallization, a material-liquid ratio of the primary crystallization product to the solvent for repeated crystallization is 1:3.5-9.5. In some typical embodiments, the material-liquid ratio of the primary crystallization product to the solvent for repeated crystallization is 1:4.5-8.5.

In some optional embodiments of the present disclosure, the inert gas includes one of helium, neon, argon, krypton, xenon, nitrogen, or carbon dioxide. In some optional embodiments of the present disclosure, the inert gas includes nitrogen or carbon dioxide.

BRIEF DESCRIPTION OF DRAWINGS

In order to more clearly illustrate the technical solutions of examples of the present disclosure, accompanying drawings which need to be used in the examples will be introduced below briefly. It should be understood that the accompanying drawings below merely show some examples of the present disclosure, and therefore should not be considered as limitation to the scope. Those ordinarily skilled in the art still could obtain other relevant accompanying drawings according to these accompanying drawings, without using creative effort.

DETAILED DESCRIPTION OF EMBODIMENTS

Implementation solutions of the present disclosure will be described in detail below with reference to embodiments and examples, while those skilled in the art could understand that the following embodiments and examples are merely used for illustrating the present disclosure, but should not be considered as limitation to the scope of the present disclosure. If no specific conditions are specified in the embodiments and examples, they are carried out under normal conditions or conditions recommended by the manufacturers. If manufacturers of reagents or apparatuses used are not specified, they are conventional products commercially available.

The preparation route of semi-synthetic dihydroquercetin with quercetin as a raw material has economic advantages and environmental advantages, and particularly can render a target product with absolute configuration consistent or nearly consistent with that of natural dihydroquercetin. This is a necessary condition for a dihydroquercetin product to enter the pharmaceutical and food fields; however, whether the semi-synthetic method is feasible, practical, and economical depends on whether the acid-base property of the reaction solvent, reagent, and reaction medium coincides with advantageous dissolution behavior of quercetin.

Since the quercetin is insoluble in water (but is easily soluble in an alkaline aqueous solution), and is slightly soluble in solvents such as lower aliphatic alcohols, aliphatic ketones, and fatty acid esters at room temperature (the solubility is also less than 1% even in boiling glacial acetic acid), in terms of feasibility and practicality, neutral and acidic water and most neutral and acidic organic solvents are not suitable as semi-synthetic reaction solvents, and particularly lack practicability and economy. Therefore, the inventors wish to be capable of implementing and completing the reduction reaction of quercetin in an alkaline aqueous solution. However, it is not easy to find a reduction reaction reagent capable of successfully reducing C ring double bond in a flavonol molecular structure in an alkaline aqueous solution.

Through a large number of experimental researches, the applicant firstly developed a sulfite binary combined reducing agent with sodium hydrosulfite as a main component to carry out the reduction reaction on quercetin dihydrate, and then carried out extraction, washing, concentration, and subsequent repeated crystallization processes on noncentrated cake product to obtain dihydroquercetin (see another patent document submitted on the same day for details). Although the foregoing method can well overcome the defects of the prior art and achieve a great progress, a slight deficiency is that component A (sodium hydrosulfite) in the combined reducing agent belongs to the category of dangerous chemical goods, and thus should not get damp during transportation, storage, and use, otherwise, there are certain safety risks; secondly, a mass ratio of the sulfite binary combined reducing agent to a starting raw material is obviously higher than that in the technical solution of the present disclosure, then on this basis, the present disclosure further has a lower cost advantage.

Considering the above reasons, the present disclosure aims at finding a novel reducing agent that is safer during storage, transportation and use, has a lower mass ratio to the starting raw material, and even is cheaper to replace the foregoing sulfite binary combined reducing agent, to reduce quercetin dihydrate to dihydroquercetin. Through further experimental researches, the applicant also invented a new semi-synthetic method of reducing quercetin dihydrate to dihydroquercetin in an alkaline aqueous solution with thiourea dioxide as a reducing agent.

Embodiments of the present disclosure and the semi-synthetic method of dihydroquercetin are illustrated below.

The semi-synthetic method of dihydroquercetin in the present disclosure includes the following steps:

adding quercetin dihydrate to purified water adjusted to be within a specified alkaline range with an alkalizing reagent, heating and stirring the quercetin dihydrate until fully dissolved, and then adding thiourea dioxide under the protection of an inert gas to perform a reduction reaction, to obtain an endpoint reduction reaction solution;

diluting the endpoint reduction solution with purified water in a specified proportion and cooling the resultant, then adding dilute acid dropwise for acidification (ring closing), followed by aging and filtration, and collecting a filtrate and a filter cake respectively;

extracting, washing, drying and concentrating the filtrate to obtain a concentrated crude product of dihydroquercetin, and then repeatedly crystallizing the concentrated crude product of dihydroquercetin to obtain the dihydroquercetin; and meanwhile, after aging and filtering the acidified reaction solution to obtain a filter cake, washing the filter cake obtained with dilute alcohol, and recycling the resultant.

In some possible embodiments of the present disclosure, in order to sufficiently improve the utilization ratio of the raw material and reduce the production cost, in the present disclosure, a simple and efficient purification treatment is performed on the filter cake obtained after aging and filtering the above acidification reaction solution, to recycle all of the filter cake (the "waste" is changed into valuable), for example, at a temperature between room temperature and 60° C., the filter cake (the unreacted quercetin dihydrate) is stirred and washed with a dilute alcohol solution having a concentration of 10%-80% for 10-30 min, so as to sufficiently extract a small amount of quercetin dihydrate contained in the filter cake, and when the liquid phase purity of quercetin in the filter cake is ≥98%, it can be reused as a starting raw material of the semi-synthetic reaction; and the dilute alcohol solution is dilute methanol or dilute ethanol. In some optional embodiments of the present disclosure, the washing temperature is room temperature to 40° C., the washing time is 15-25 min, and the concentration of alcohol in the dilute alcohol solution is 20%-60%.

The process of reduction reaction of quercetin dihydrate in the present disclosure is as follows:

The present disclosure significantly differs from the prior art in that: in the present disclosure, quercetin dihydrate or anhydrous quercetin is firstly dissolved in an alkaline aqueous solution, and under the protection of an inert gas, the present disclosure uses thiourea dioxide as a reducing agent to reduce quercetin dihydrate to dihydroquercetin for the first time, which is one of the main innovative points of the present disclosure.

A special advantage of the semi-synthetic method of dihydroquercetin of the present disclosure is that trans configuration accounts for up to 99% or more in a dihydroquercetin product obtained, and is consistent with that of natural dihydroquercetin.

The quercetin dihydrate is added to an alkaline aqueous solution, the resultant is heated and stirred until fully dissolved, and then under the protection of an inert gas, the quercetin dihydrate is reduced to dihydroquercetin in one step with thiourea dioxide as the reducing agent; and the reduction reaction condition of adding the thiourea dioxide in two times is disclosed.

As described in the above, in some embodiments, the solvent water is salt-free water, including purified water, deionized water, or distilled water. In some typical embodiments, the salt-free water is purified water. In some embodiments, a mass ratio of the quercetin dihydrate to the reaction solvent water is 1:120-220, such as 1:140-200, 1:160-180, or 1:165-175, for example, 1:120, 1:130, 1:140, 1:150, 1:160, 1:170, 1:180, 1:190, 1:200, 1:210, or 1:220.

In some embodiments, the alkalizing reagent may be at least one of sodium carbonate, potassium carbonate, and calcium carbonate, optionally at least one of sodium carbonate and potassium carbonate. In some embodiments, a molar ratio of the quercetin dihydrate to the alkalizing reagent is 1:3.5-6.5, such as 1:3.5, 1:4.0, 1:4.5, 1:5.0, 1:5.5, 1:6.0 or 1:6.5, optionally 1:4.5-5.5.

In some embodiments, a molar ratio of the quercetin dihydrate to the thiourea dioxide is any ratio in 1:2.5-7.5, such as 1:2.5, 1:3.0, 1:3.5, 1:4.0, 1:4.5, 1:5.0, 1:5.5, 1:6.0, 1:6.5, 1:7.0 or 1:7.5. In typical embodiments, the molar ratio of the quercetin dihydrate to the thiourea dioxide is 1:3.0-7.0. In more typical embodiments, the molar ratio of the quercetin dihydrate to the thiourea dioxide is 1:3.5-6.5. In some embodiments of the present disclosure, the thiourea dioxide may be added to the reduction reaction solution in one or more times; and if it is added in two times, an addition amount in the first time is ⅔ to ⅘ of the total amount of the thiourea dioxide, and an addition amount in the second time is ⅕ to ⅓ of the total amount of the thiourea dioxide.

The thiourea dioxide is quite stable in property in acidic, neutral, and room temperature conditions and thus can be stored for a long period of time. However, under alkaline and heating conditions, the thiourea dioxide is rapidly decomposed into the form of formamidine sulfinic acid ($CH_4N_2O_2S$), which is very active, and rapidly decomposed into urea and sulfenic acid (H—O—S—O—H) under alkaline conditions. The sulfenic acid is a very strong reducing agent, has a very high reduction potential (−1000 to −1200 mv), and the reducing capacity is obviously higher than that of sodium thiosulfate. The present disclosure reduces quercetin (or dihydrate) to dihydroquercetin in an alkaline aqueous solution by using the strong reducing property of sulfenic acid. In the reduction reaction process, the applicant effectively inhibits the generation of by-products by using the measure of inert gas protection and setting the pH value of the reaction solution in a preferred range. In order to facilitate those skilled in the art to repeat the semi-synthetic method of the present disclosure, the reaction temperature and the reaction time of the reduction reaction are exemplified below: the reaction temperature of the reduction reaction may be 60-100° C., optionally 70-90° C.; and the reaction time of the reduction reaction may be 60-120 min, optionally 70-110 min.

In order to facilitate those skilled in the art to repeat the semi-synthetic method of the present disclosure, the use of inert gas (including inactive gas), such as helium, neon, argon, krypton, xenon, nitrogen or carbon dioxide, is illustrated below. In practical operation of the present disclosure, nitrogen or carbon dioxide is often used.

In order to facilitate those skilled in the art to repeat the semi-synthetic method of the present disclosure, a manner of adding the thiourea dioxide in two times is illustrated below: in practical operation of the present disclosure, the addition amount in the first time is ⅔ to ⅘ of the total amount of the thiourea dioxide, and the addition amount in the second time is ⅓ to ⅕ of the total amount of the thiourea dioxide. Further illustration is made below. The temperature and time of adding the thiourea dioxide to the reduction reaction solution of quercetin dihydrate to carry out the reduction reaction are respectively as follows: the reaction temperature after the first addition is 70-85° C., such as 75° C. or 80° C., and the reaction temperature after the second addition is 85-95° C.; time of a first stage of reduction reaction is 75-85 min, such as 80 min, or 82 min, etc., and time of a second stage of reduction reaction is 25-35 min. When the second stage of reduction reaction reaches the endpoint, the reaction solution is immediately subjected to vacuum suction into another pre-cooled reaction flask, into which a formulated amount of purified water is immediately pumped, and the resultant is rapidly stirred to cool down, so as to stop the reaction as soon as possible.

In order to facilitate those skilled in the art to repeat the semi-synthetic method of the present disclosure, control indexes of type, concentration, and pH value of acidification endpoint of the dilute acid used in the acidification (ring closing) process in step 2 are illustrated below: the dilute acid may be dilute hydrochloric acid, dilute sulfuric acid, or dilute acetic acid, etc.; in the following illustration of the embodiments of the present disclosure, the dilute hydrochloric acid having a concentration of 3.0 mol/L is used; without doubt, the concentration also may be any concentration in the range of 1-4.0 mol/L, such as 1.0 mol/L, 2.0 mol/L, 3.0 mol/L, and 4.0 mol/L. The pH value of the acidification endpoint is any value in 0.5-3.5, such as 1.5, 2.0, 2.5 or 3.0.

In practical operation, in order to make the unreacted quercetin dihydrate precipitate more sufficiently, after the acidification is finished, the acidified material solution is subjected to moderate aging (standing), for example, aging for a time value within 0.5-4 h such as 0.5 h, or 1 h, or 2 h, or 3 h. After aging, solid-liquid separation can be performed by using a method such as vacuum filtration, or pressure filtration, or centrifugation separation, to obtain a clear filtrate and a filter cake, respectively.

In practical operations, in order to sufficiently improve the utilization rate of starting raw material and reduce the production costs, in the present disclosure, the filter cake after filtration is timely purified, or subjected to one-time purification after centralized collection, for example, at room temperature to boiling temperature of the dilute alcohol (e.g., 25° C., or 30° C., or 45° C., or 50° C., or 65° C., etc.), the filter cake (the unreacted quercetin dihydrate, in which a small amount of dihydroquercetin is contained) is stirred and washed with the dilute alcohol solution with a concentration of 10%-70%, such as 20%, 30%, 40%, 50%, or 60% (the washing may last for 8 min, or 9 min, or 10 min), so that a small amount of dihydroquercetin contained in the filter cake is sufficiently extracted, and when the liquid phase purity of the quercetin dihydrate in the filter cake is ≥99%, it can be recycled as a starting raw material of the semi-synthetic reaction.

In practical operations, the extraction process in the present disclosure is three times of extraction by using a hydrophobic organic extracting agent, that is, the acidified filtrate and the hydrophobic organic extracting agent are poured into a separating funnel in three times according to a mass ratio of 1:0.1-1:1.0 for three times of shaking extraction. Without doubt, a mixing mass ratio of the acidified filtrate to the hydrophobic organic extracting agent also may be 1:0.1-1:0.8, such as 1:0.1, 1:0.2, 1:0.3, 1:0.4, 1:0.5, 1:0.6, or 1:0.7. In order to facilitate those skilled in the art to better repeat the method of the present disclosure, the hydrophobic organic extracting agent is illustrate below. The hydrophobic organic extracting agent may be at least one of an aliphatic ether, an alicyclic ether, an aliphatic ester, and a hydrophobic aliphatic ketone. In some embodiments, the hydrophobic organic extracting agent may be at least one of an aliphatic ether, an aliphatic ester, and a hydrophobic aliphatic ketone. In some embodiments, the hydrophobic organic extracting agent may be tert-butyl ether, isopropyl ether, ethyl acetate, isopropyl acetate, and methyl isobutyl ketone, etc.

After completing three times of extraction operation, the extract solutions are combined in the separating funnel, washed by shaking once with 150-350 ml of purified water, and then washed by shaking once with 100-300 ml of 15% aqueous sodium chloride solution. After the washing is completed, a water layer is separated completely, a drying agent is added to perform dehydration, and after the water-containing drying agent is filtered, a dehydrated extract solution is obtained; the drying agent may be anhydrous sodium sulfate, anhydrous magnesium sulfate, anhydrous copper sulfate, anhydrous calcium chloride, or a molecular sieve, etc.; and in practical operations of the present disclosure, anhydrous sodium sulfate or anhydrous magnesium sulfate is often used. The dehydrated extract solution is subjected to vacuum concentration, wherein a concentrating temperature may be any temperature in 60° C.-80° C., and degree of vacuum may be any degree of vacuum in 650-750 mmHg.

After the above extraction, washing, drying, and concentration, a semi-synthetic crude product of dihydroquercetin can be obtained. In this case, the liquid phase purity thereof is about 80%. In order to further improve the purity thereof, the present disclosure repeatedly crystallizes the above crude product in an alcohol-water mixed solvent. In practical operations, in the present disclosure, the semi-synthetic dihydroquercetin crude product and the solvent for repeated crystallization are sequentially added to a round bottom flask with a condenser, heated in a water bath, and stirred until fully dissolved, then activated carbon is added to reflux and decolorize, the resultant is filtered while it is hot, and the decolorized filtrate is transferred into a crystallization flask, and slowly cooled to 10° C.-5° C. while being slowly stirred, and stands for crystallization for an appropriate period of time, and then the resultant is filtered and washed to obtain a dihydroquercetin primary crystallization product with a liquid phase purity of ≥95%; after completely appropriately adjusting the alcohol concentration and the solvent ratio in the solvent for repeated crystallization in the primary crystallization process, secondary crystallization is performed on the primary crystallization product, and a dihydroquercetin secondary crystallization product is obtained, i.e. dihydroquercetin with a liquid phase purity of ≥99%. In order to facilitate those skilled in the art to repeat the method of the present disclosure, the use amount and composition of the solvent for repeated crystallization are illustrated below: a material-liquid ratio of the concentrated crude product to the solvent for repeated crystallization is 1:3.0-10.0, optionally 1:5.0-8.0; the solvent for repeated crystallization may be a mixed solvent of purified water and a lower aliphatic alcohol such as methanol, ethanol, and isopropanol; in practical operation, the present disclosure often uses a mixed solvent of methanol or ethanol and purified water, wherein a volume ratio of methanol/ethanol to purified water may be any ratio in 1:0.1-0.9, such as 1:0.1, 1:0.2, 1:0.3, 1:0.4, 1:0.5, 1:0.6, 1:0.7, 1:0.8, or 1:0.9. In the corresponding alcohol-water mixed solvent, the alcohol concentration ranges 10%-90%, for example, 10%, 20%, 30%, 40%, 50%, 60%, 70%, 80%, or 90%. Optionally, the concentration of methanol or ethanol in the mixed solvent ranges 20%-80%; more optionally, the concentration of methanol or ethanol in the mixed solvent ranges 30%-70%.

The liquid chromatography conditions for the reduction reaction crude product, primary crystallization product, and secondary crystallization product are as follows:

chromatography column: Intertsustain C18, 250*4.6, 5 μm, CN-6020-07346, S/N5JR98073;

mobile phase: A pump—0.1% phosphoric acid aqueous solution, B pump—methanol;

gradient method: flow rate—1.5 ml/min, sample size—10 A, column temperature—40° C., detection wavelength—290 nm; and concentration of sample for test: 0.5 mg/ml.

Compared with the prior art, the present disclosure uses the thiourea dioxide as the reducing agent for chemical conversion of natural flavonol compounds (such as quercetin dihydrate) to flavanonol compounds (such as dihydroquercetin).

The present disclosure skillfully fuses "relatively strong reducing activity of thiourea dioxide under alkaline conditions" and "the characteristic that quercetin can be completely dissolved in an alkaline aqueous solution", and elaborately designs appropriate conditions of reduction reaction, liquid-solid separation, liquid-liquid extraction, and repeated crystallization of the crude product, thus obtaining unexpected technical effects.

In addition, in the present disclosure, the unreacted quercetin dihydrate (filter cake) in the reduction reaction is also purified conveniently and effectively, and it is allowed to be recycled repeatedly, thus greatly reducing the costs of semi-synthesis to a larger extent.

Compared with the sodium hydrosulfite reducing agent, the thiourea dioxide in the present disclosure is very stable in properties under neutral and acidic conditions, is more conducive to storage and transportation, and is cheaper than sodium hydrosulfite. In view of the fact that the thiourea dioxide is quite active under alkaline conditions, a measure of inert gas protection is used in the heating reaction, so as to inhibit the production of by-products to the greatest extent.

The semi-synthetic method of dihydroquercetin in the present disclosure is further described in detail below in conjunction with the examples.

The liquid chromatography conditions for the reduction reaction crude product, primary crystallization product, and secondary crystallization product in the following examples and comparative examples are as follows:

chromatography column: Intertsustain C18, 250*4.6, 5 μm, CN-6020-07346, S/N5JR98073;

mobile phase: A pump—0.1% phosphoric acid aqueous solution, B pump—methanol;

gradient method: flow rate of 1.5 ml/min, sample size of 10 μL, column temperature of 40° C., detection wavelength of 290 nm; and concentration of sample for test: 0.5 mg/ml.

Information about main instrument used in the following Examples 1-11 and Comparative Examples 1-2 is as shown in Table 1, and information about raw materials, reagents, and solvents used is as shown in Table 2:

TABLE 1

| Instrument name | Model/ Specification | Instrument No. | Manufacturer |
|---|---|---|---|
| Electronic balance | B3002 | YHA009 | Shanghai Liangping Instrument Company |
| pH measuring system | M400 | / | METTLER TOLED (Shanghai) Co., Ltd. |
| Constant speed electric mixer | JJ-2Q | / | Changzhou Guoyu Instrument Manufacturing Co., Ltd. |
| Vacuum drying oven | DZF-6050 | B61016 | Shanghai Boxun Experiment Co., Ltd. |
| Vacuum filter | 1000 × 500 ml | / | Shanghai Glass Instrument Co., Ltd. |

TABLE 2

| Name | Specification | Purity | Manufacturer |
|---|---|---|---|
| Quercetin dihydrate | Pharmaceutical grade | ≥95% | Shaanxi Jiahe Phytochem Co., Ltd. |

TABLE 2-continued

| Name | Specification | Purity | Manufacturer |
|---|---|---|---|
| Thiourea dioxide | Analytically pure | ≥96.0% | Macklin Company |
| Anhydrous sodium carbonate | Analytically pure | ≥99.0% | Sinopharm Shanghai Chemical Reagent Co., Ltd. |
| Purified water | Meet GMP standards | / | Enterprise self-made |
| Hydrochloric acid | Reagent grade | 35.0%-38.0% | Yangzhou Hubao Chemical Reagent Co., Ltd. |
| Methyl isobutyl ketone | Industrial premium product | ≥99% | Sinopharm Shanghai Chemical Reagent Co., Ltd. |
| Sodium chloride | Reagent grade | ≥99% | Sinopharm Shanghai Chemical Reagent Co., Ltd. |
| Anhydrous sodium sulfate | Reagent grade | ≥99% | Sinopharm Shanghai Chemical Reagent Co., Ltd. |
| Ethanol | Pharmaceutical grade | ≥95% | Xuzhou Xiangpei |
| Activated carbon | Reagent grade | 99.99% | Shanghai Activated Carbon Co., Ltd. |

In the present disclosure, the molar ratio/mass ratio of the quercetin dihydrate (referred to as a starting raw material X for short in Table 3) to the reducing agent (thiourea dioxide is referred to as A for short, and sodium hydrosulfite is referred to as B for short in Table 3), the pH value in the reduction reaction process, the reduction reaction temperature and reaction time, and whether to implement the inert gas protection are used as variable conditions, listed in Table 3:

TABLE 3

| Implementation No. | Molar ratio of starting raw material to reducing agent | Range of pH value in first stage of reduction reaction process | Temperature of first stage of reduction reaction (° C.) | Time of first stage of reduction reaction (min) | Temperature of second stage of thermal insulation reaction (° C.) | Time of second stage of thermal insulation reaction (min) |
|---|---|---|---|---|---|---|
| Example 1 | X:A = 1:5.0 | 9.5-11.5 | 75 | 75 | 85 | 30 |
| Example 2 | X:A = 1:5.0 | 9.5-11.5 | 75 | 75 | 85 | 30 |
| Example 3 | X:A = 1:6.5 | 9.5-11.5 | 75 | 75 | 85 | 30 |
| Example 4 | X:A = 1:3.5 | 9.5-11.5 | 75 | 75 | 85 | 30 |
| Example 5 | X:A = 1:5.0 | 10.5-12.5 | 75 | 75 | 85 | 30 |
| Example 6 | X:A = 1:5.0 | 8.5-10.5 | 75 | 75 | 85 | 30 |
| Example 7 | X:A = 1:5.0 | 9.5-11.5 | 80 | 85 | 85 | 30 |
| Example 8 | X:A = 1:5.0 | 9.5-11.5 | 70 | 70 | 85 | 30 |
| Example 9 | X:A = 1:5.0 | 9.5-11.5 | 75 | 75 | 90 | 25 |
| Example 10 | X:A = 1:5.0 | 9.5-11.5 | 75 | 75 | 80 | 35 |
| Comparative Example 1 | X:B = 1:5.0 | 9.5-11.5 | 75 | 75 | 85 | 30 |
| Comparative Example 2 | X:A = 1:5.0 | 9.5-11.5 | 75 | 75 | 85 | 30 |

In the table above, Example 2 is a reduction reaction example in which amounts put-in of the raw material, the solvent, the alkalizing agent, and the reducing agent in Example 1 are enlarged by five times.

The main operation steps and relevant fixed technical conditions of the above Examples 1-10 and Comparative Examples 1-2 are as follows:

Step 1: Reduction Reaction 3500 ml of purified water and 28.0 g of anhydrous sodium carbonate were added to a reaction flask. The mixture was continuously stirred until pH was stable, and heated in a water bath to 70° C. A nitrogen flow was introduced (no nitrogen flow needs to be introduced in Comparative Example 2). 20 g of quercetin dihydrate was added. The mixture was stirred until fully dissolved, and then continued to be heated until reaching the temperature in the first stage of reduction reaction in each of the examples and comparative examples. The reducing agent accounting for ¾ of the total amount of thiourea dioxide in each of the examples and comparative examples was added to perform the first stage of reduction reaction. After the reaction was completed, when the temperature was increased to the temperature required for the second stage of reduction reaction, the remaining ¼ of the reducing agent was added to perform the second stage of reduction reaction. When the reaction reached the endpoint, the heating was immediately stopped, and 700 ml of purified water was rapidly added to dilute the reaction solution, meanwhile, stirring was started and cool circulating water was used for cooling, to obtain the endpoint reduction reaction solution.

Step 2: Acidizing, Aging, and Filtering

After the reduced reaction solution diluted in step 1 was cooled to 20° C., 3 mol/L of dilute hydrochloric acid was uniformly added dropwise in a state of being continuously cooled and stirred, to acidify the reduced reaction solution to pH 2.0-2.5. When the pH value was stable and unchanged, the resultant stood and was aged for 2.5 h, and then filtered, to obtain a clear acidic filtrate containing dihydroquercetin, which stood for later use.

P.S.: Washing and Purifying the Acidified Filter Residue:

The filter residue was scraped from the funnel and transferred into a flask, 35% dilute ethanol having the volume equivalent to 20 times the weight of the dry filter residue and preheated to 50° C. was added, and the mixture was continuously stirred and washed for 15 min, and then was subjected to vacuum filtration; the filter cake was then rinsed once by using 35% dilute ethanol having a 5-time volume at the same temperature. After sufficient drying, the resultant was transferred into an air-blast drying cabinet, and dried at a drying temperature of 80-105° C. for 4 h to obtain quercetin dihydrate with purity of 98.0% or higher, which was recycled as a starting raw material of the reduction reaction for reuse.

Step 3: Extracting, Washing, Drying, and Concentrating

All the acidified filtrate in step 2 was poured into a separating funnel, and dihydroquercetin was extracted by shaking in 3 times with a total amount of 1100 ml methyl isobutyl ketone (volumes in the 3 times are 500 ml, 350 ml, and 250 ml, respectively). The extract solutions in the 3 times were combined and washed once with 250 ml of purified water and 200 ml of 15% aqueous sodium chloride solution in sequence. After the water layer was separated completely, 30 g of anhydrous sodium sulfate was added thereto, the resultant was shaken for 5 min, and then stood to dry for 2.5 hr, then the sodium sulfate was filtered off, the dehydrated filtrate was concentrated under the conditions of 60-80° C. water bath and the vacuum degree of 700-750 mmHg until no droplets dripped out, then 30 ml of ethanol was added. After the solid was completely dissolved by rotary shaking, concentration was continued for 25 min to obtain a light yellow honeycomb semi-synthetic dihydroquercetin concentrated crude product, which was weighed and sampled for liquid phase purity detection.

Step 4: Repeated Crystallization (Recrystallization)

Primary crystallization: a specified amount of semi-synthetic concentrated crude product was put into a round bottom flask with a reflux condenser, an ethanol-purified water mixed solvent with an ethanol concentration of 45% and a volume 6.0 times that of the crude product was added, then the mixture was stirred and heated in a water bath until fully dissolved, activated carbon equivalent to 0.5% of semi-synthetic crude product by mass was added, followed by refluxing and decolorization for 10 min, the resultant was filtered while being hot, and the filter cake was washed twice with 15 ml of dilute ethanol with the same concentration precooled to 5° C. (volumes in the two times were 10 ml and 5 ml, respectively). The filtrate and a washing liquid were combined, and transferred together into a crystallization flask, slowly cooled to 8° C. or lower under slow stirring, and after being allowed to stand and crystallize at 8-5° C. for 2 h, the resultant was subjected to vacuum filtration, and the filter cake was stirred and washed twice with 17 ml of dilute ethanol with the same concentration precooled to 5° C. or lower (volumes in the two times were 10 ml and 7 ml, respectively). After sufficient drying, a wet crystallization substance was placed in a vacuum drying oven, and dried in vacuum at 50-60° C. to dry, to obtain a primary dihydroquercetin crystallization product with a purity of ≥95%.

Secondary crystallization: weighed primary crystallization product was placed in a decolorizing bottle, ethanol-water mixed solvent with a volume 7.5 times mass of the primary crystallization product and an ethanol concentration of 55% was added, and then decolorizing, filtering, cooling crystallization, filtering, and vacuum drying were successively carried out according to the primary crystallization method to obtain a secondary dihydroquercetin crystallization product with a liquid phase purity of ≥99%.

TABLE 4

Crude Product Output, Yield, Liquid Phase Purity, and Relevant Material Results under Reduction Reaction Conditions in Various Examples and Comparative Examples in Table 3

| Example No. | Concentrated crude product output | Liquid phase purity of concentrated crude product | Recycling amount of quercetin dihydrate | Recycling rate of quercetin dihydrate | Reduction reaction pure yield | Number of impurities | Maximum single impurity area percentage | Total impurity area percentage |
|---|---|---|---|---|---|---|---|---|
| Example 1 | 15.54 g | 79.03% | 3.38 g | 16.90% | 86.48% | 9 | 6.29% | 20.97% |
| Example 2 | 77.96 g | 78.45% | 16.92 g | 16.92% | 86.09% | 9 | 6.37% | 21.55% |
| Example 3 | 16.30 g | 63.45% | 2.60 g | 13.00% | 69.51% | 12 | 8.51% | 36.55% |
| Example 4 | 12.31 g | 68.57% | 6.46 g | 32.30% | 72.91% | 11 | 8.02% | 31.43% |
| Example 5 | 16.14 g | 66.96% | 3.62 g | 18.1% | 77.16% | 11 | 8.30% | 33.04% |
| Example 6 | 13.29 g | 69.11% | 6.61 g | 33.05% | 80.22% | 11 | 7.93% | 30.89% |
| Example 7 | 17.09 g | 72.87% | 3.75 g | 18.75% | 89.63% | 10 | 7.57% | 27.13% |
| Example 8 | 15.19 g | 74.11% | 4.01 g | 20.05% | 82.34% | 10 | 7.17% | 23.13% |
| Example 9 | 17.10 g | 73.01% | 2.46 g | 12.30% | 83.24% | 10 | 7.31% | 26.99% |
| Example 10 | 16.45 g | 72.46% | 3.03 g | 15.15% | 82.15% | 10 | 7.43% | 27.54% |
| Comparative Example 1 | 10.29 g | 48.29% | 9.01 g | 45.05% | 52.88% | 26 | 11.83% | 52.95% |
| Comparative Example 2 | 15.87 g | 75.87% | 3.18 g | 15.90% | 83.72% | 15 | 7.67% | 24.13% |

Notes:
1) The starting raw material quercetin dihydrate has the molar mass of 338.27, and the content of 95.0%, and the molar mass of dihydroquercetin is 304.25; and
2) the feeding amounts of respective raw materials, reagents, and solvents in Example 2 are five times those in Example 1.

It can be seen from Table 4 that:

(1) Compared with Example 1, when other reaction conditions are not changed and only sodium hydrosulfite is used as the reducing agent in place of thiourea dioxide, various index parameters such as the reduction crude product output, the liquid phase purity of the crude product, the pure yield, and the number of impurities in Comparative Example 1 are all significantly changed, and become quite bad. It is thus indicated that: (a) as a single reducing agent, the use of thiourea dioxide is far superior to the use of sodium hydrosulfite as a reducing agent; and (b) only when combined with sodium pyrosulfite in a certain proportion, sodium hydrosulfite can exert a reduction reaction effect comparable to that of thiourea dioxide alone.
(2) As a comparative example (Comparative Example 2) of Example 1, when other conditions are unchanged and the inert gas protection is dispensed with merely during the reaction, although various index levels have small changes, the overall index result is obviously lower than that of Example 1; the experimental results of Comparative Example 2 indicate that the inert gas protection measure is quite necessary when thiourea dioxide is used as the reducing agent. Under the conditions of the same ratio of the solvent to the alkalizing agent and the same reaction temperature and time as in Example 1, in Examples 3 and 4, after the molar ratio (1:5.0) of the starting raw material quercetin dihydrate to the thiourea dioxide fluctuates by 30%, the concentrated crude product output, the liquid phase purity of the crude product (corresponding index levels are total impurity and maximum single impurity area percentages, and the same below), the pure yield level, and the number of impurities are all changed to different degrees (get worse), but Examples 3 and 4 still have better liquid phase purity and pure yield level; from the overall level, various index levels of Examples 3 and 4 are not as good as Examples 1 and 2. Therefore, it is more suitable to fix the parameter molar ratio of the starting raw material quercetin dihydrate to the thiourea dioxide at 1:5.0.
(3) Under the same conditions of the molar ratio of the solvent to the main materials as well as the reaction temperature and time, in Examples 5 and 6, after the pH value (9.5-11.5, corresponding process parameter is proportion of the alkalizing reagent) of the reaction process in Example 1 is floated up (Example 5) and down (Example 6) by one pH unit, the concentrated crude product output, the liquid phase purity of the crude product, the pure yield level, and the number of impurities and area percentage are all decreased to different degrees (get worse), but the decrease magnitudes are still at an acceptable level. Upon overall comparison, the set parameters of pH value of the reaction processes in Examples 1 and 2 are more appropriate than those in Examples 5 and 6.
(4) Under the conditions of the same solvent proportion, the same main material proportion, and the same reaction pH value as those in Examples 1 and 2, up-regulating or down-regulating the first and second stages of reaction temperatures and time within a relatively small range (Examples 7-10) will also result in slight decrease in index level of the purity of the crude product and the impurity (but still at an acceptable good level), wherein the decrease of yield level in Examples 8-10 is smaller and the yield level in Example 7 is in turn higher than those in Examples 1-2. The above results also indicate that the influence of slight fluctuations of reaction temperature and time parameters during the reduction reaction on the reaction yield and crude product purity is less than that of the ratio of the starting raw material to the reducing agent.

TABLE 5

Experimental Results of Primary Recrystallization of Reduction Reaction Crude Products in Some Examples in Table 4

| Implementation No. | Mass of crude product input | Purity of crude product input | Primary crystallization substance output | Liquid phase purity of primary crystallization substance | Yield of primary crystallization substance (pure yield) |
|---|---|---|---|---|---|
| Example 1 | 15.0 g | 79.03% | 11.29 g | 95.51% | 90.96% |
| Example 2 | 75.0 g | 78.45% | 56.01 g | 95.46% | 90.87% |
| Example 3 | 15.0 g | 63.45% | 10.58 g | 79.13% | 87.96% |
| Example 5 | 15.0 g | 66.96% | 10.78 g | 82.56% | 88.61% |
| Example 7 | 15.0 g | 72.87% | 11.08 g | 88.73% | 89.94% |
| Comparative Example 1 | 10.0 g | 48.29% | 5.21 g | 63.15% | 68.13% |
| Comparative Example 2 | 15.0 g | 76.87% | 11.0 g | 92.84% | 88.57% |

TABLE 6

Experimental Results of Secondary Crystallization of Primary Crystallization Products in Various Examples and Comparative Examples in Table 5

| Implementation No. | amount of primary crystallization substance input | Liquid phase purity of primary crystallization substance input | Output of secondary crystallization substance | Liquid phase purity of secondary crystallization substance | Number of impurities | Total impurity area percentage (%) | Yield of secondary crystallization (pure yield) |
|---|---|---|---|---|---|---|---|
| Example 1 | 10.0 g | 95.51% | 8.03 g | 99.46% | 5 | 0.54% | 83.62% |
| Example 2 | 50.0 g | 95.46% | 40.70 g | 99.44% | 5 | 0.56% | 84.79% |
| Example 3 | 10.0 g | 79.13% | 7.21 g | 91.76% | 8 | 8.24% | 83.61% |
| Example 5 | 10.0 g | 82.56% | 7.36 g | 93.91% | 7 | 6.09% | 83.72% |
| Example 7 | 10.0 g | 88.73% | 7.74 g | 96.37% | 6 | 3.63% | 84.06% |
| Comparative Example 1 | 5.0 g | 63.15% | 2.52 g | 80.49% | 16 | 19.51% | 64.24% |
| Comparative Example 2 | 10.0 g | 92.84% | 7.97 g | 97.91% | 7 | 2.09% | 84.05% |

It can be seen from the result data shown in the above Table 5 and Table 6 that:

(1) Results of Examples 1 and 2 indicate that under the same crystallization conditions, when the liquid phase purity of the crude product reaches 78% (or at least ≥75.0%) or higher, under the conditions of repeated crystallization established in the present case, the purity of the primary and secondary crystallization products obtained reaches relatively ideal levels of 95.0% and 99.0% or higher, respectively, the corresponding total average molar yields of primary and secondary recrystallization are respectively 24 90.0% and ≥83.5%. If the output of concentrated recycling product of crystallization mother liquor in the two crystallization processes is calculated, the total yield can be further increased by 7-8 percentage points, and the result is better.

(2) The results of Example 5 indicate that under the same conditions of repeated crystallization as those in Example 1 and Example 2, when the liquid phase purity of the crude product is 66.96% (see Table 4), the primary and secondary crystallization products obtained have the purity of 82.56% and 93.91%, respectively, even if the crystallization is performed once again, the product purity can only reach a level of about 97%, therefore, when the purity of the crude product is too low (correspondingly, the total impurity area percentage is too high), the crude product needs to undergo four crystallization processes, or two crystallization processes plus one polyamide column chromatography separation process, then the liquid phase purity of the final product can reach 99% or higher levels.

(3) Under the same conditions of repeated crystallization as those in Example 1 and Example 2, when the liquid phase purity of the crude product is at the level between 67% and 75%, to prepare a high-purity product of 99% or higher, three crystallization processes need to be carried out.

(4) The reduced crude product in Comparative Example 1 is derived from the crude product of the reduction reaction in Comparative Example 1 (sodium hydrosulfite as a reducing agent) in Table 1. As the purity of the crude product is too low (48.29%), according to the same crystallization conditions as those in Example 1, after two times of crystallization, the purity of the final product only can reach a level of 80%, on this basis, the product needs to be crystallized twice again, and the highest purity only can reach about 98%. After such tedious processes, the application value has obviously been lost.

Figure 1:
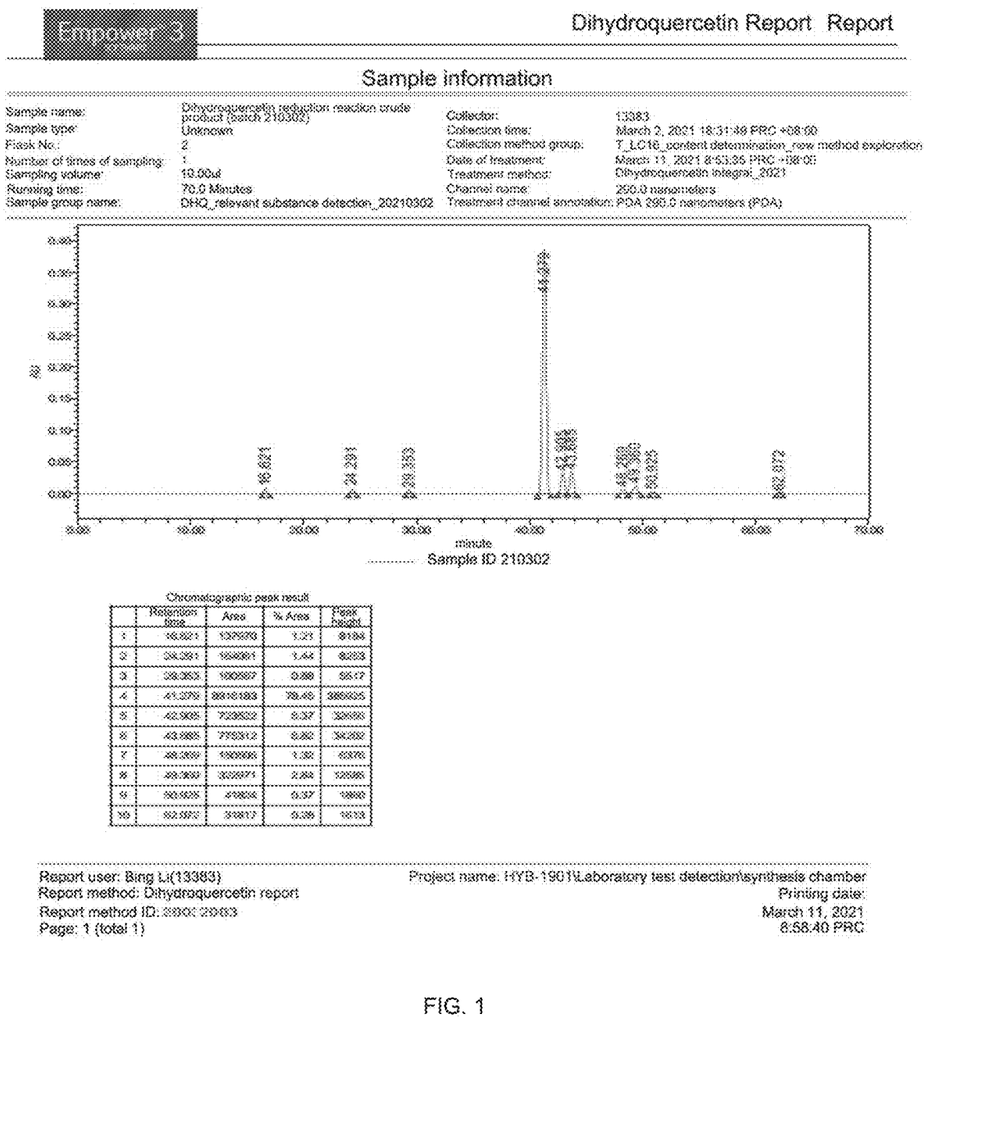
FIG. 1 is a liquid chromatogram of a semi-synthetic concentrated crude product in Example 2.
Figure 2:
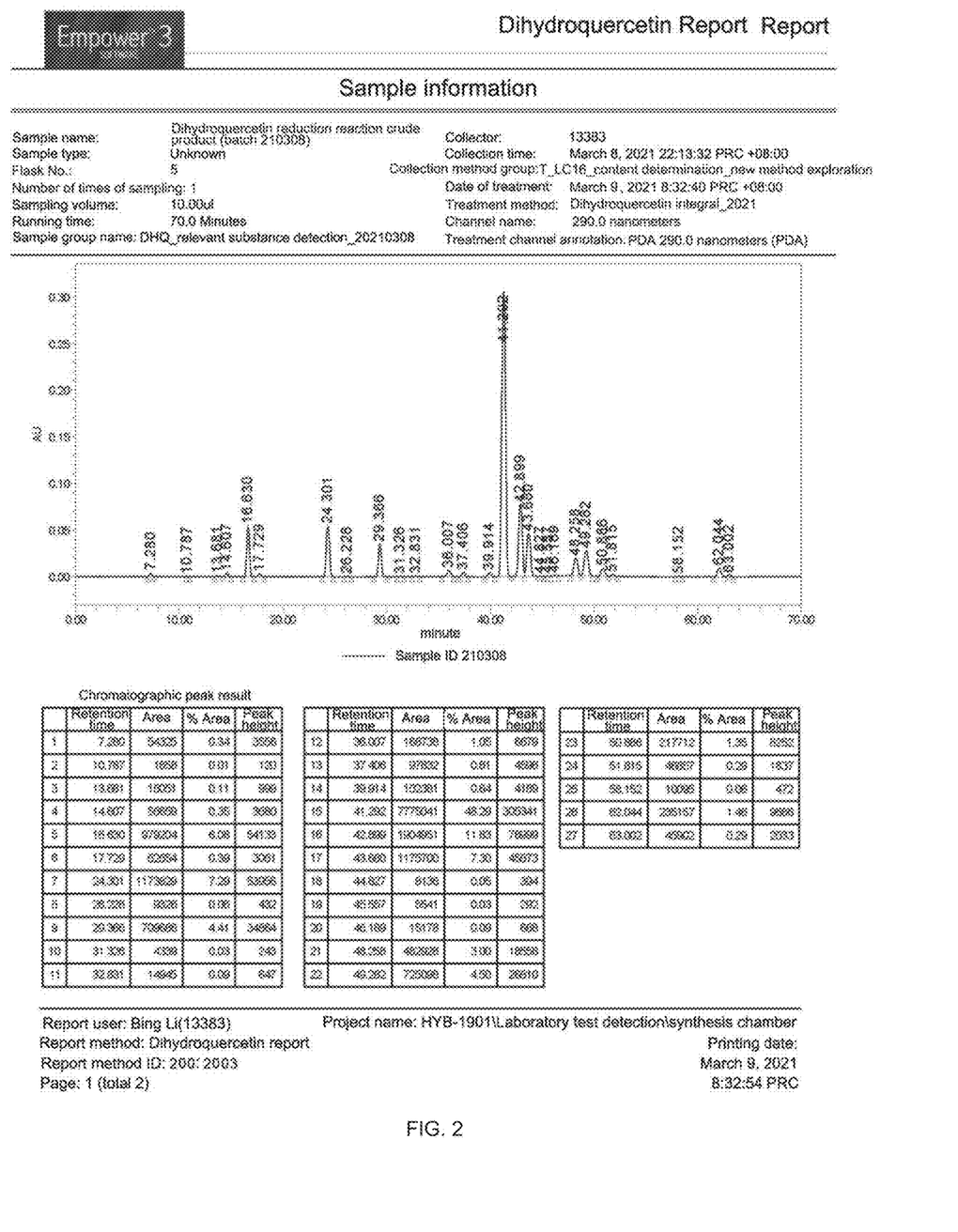
FIG. 2 is a liquid chromatogram of a semi-synthetic concentrated crude product in Comparative Example 1.
Figure 3:
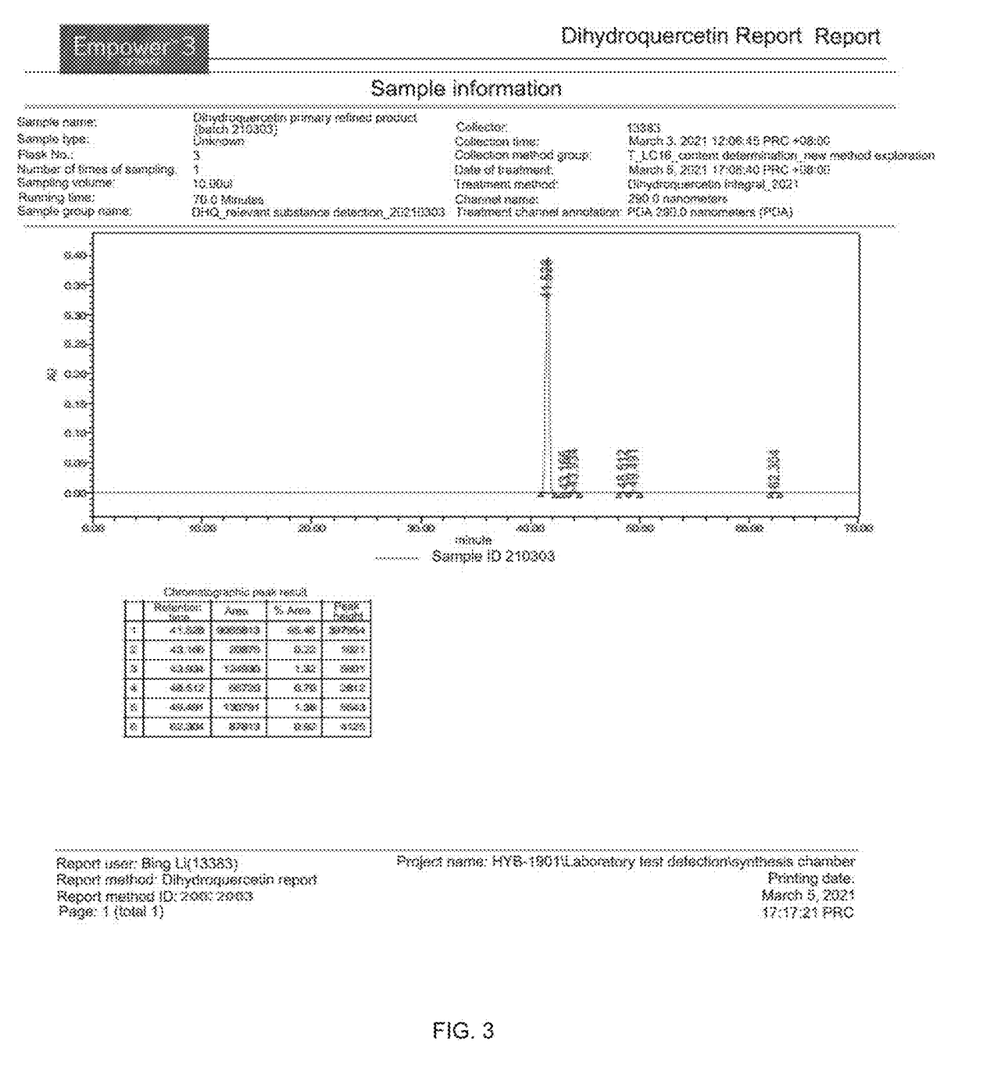
FIG. 3 is a liquid chromatogram of a primary crystallization sample in Example 2.
Figure 4:
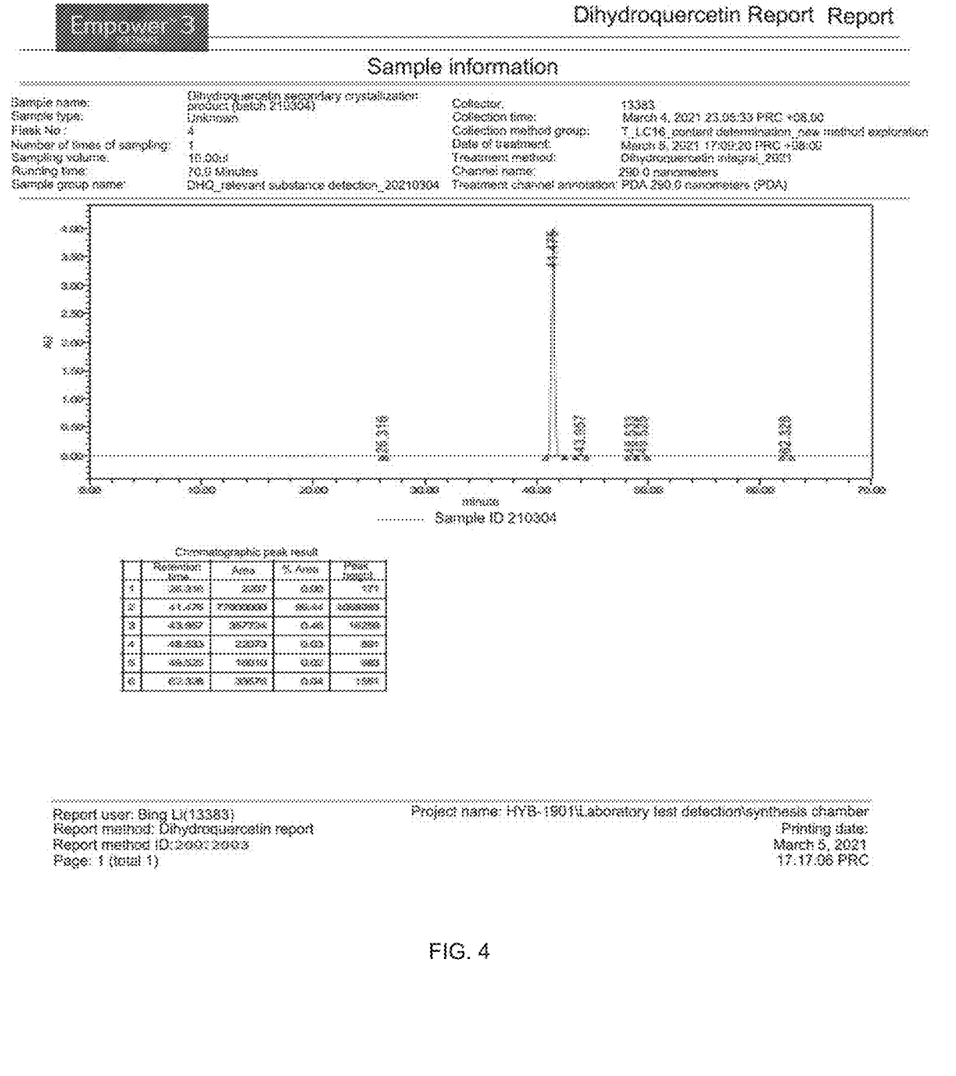
FIG. 4 is a liquid chromatogram of a secondary crystallization sample in Example 2.
Figure 5:
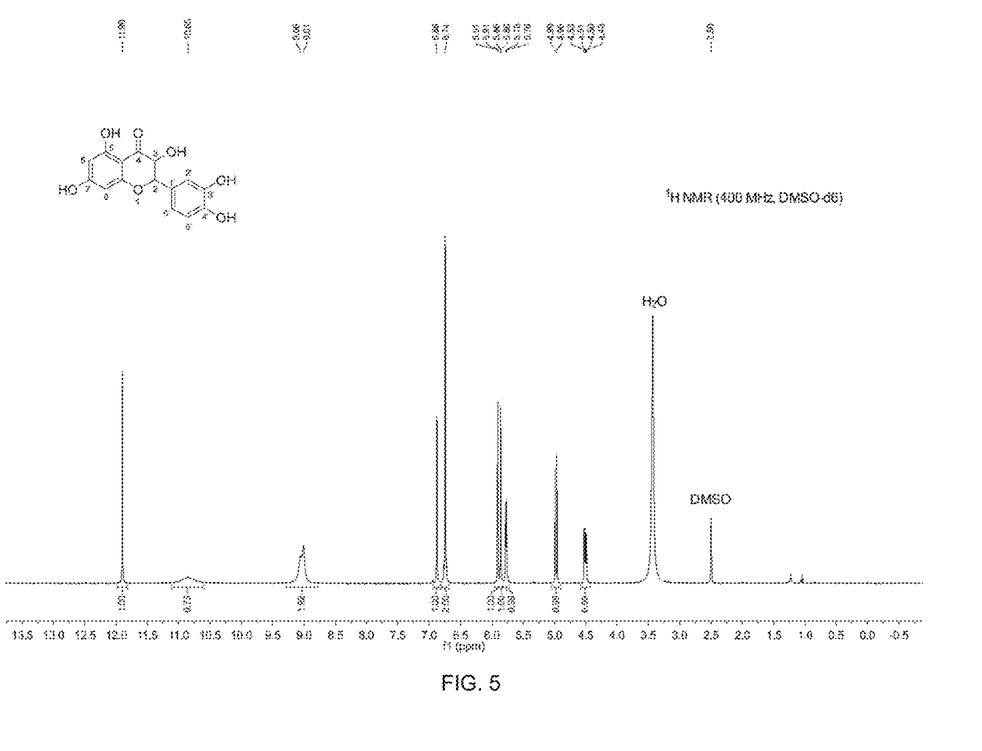
FIG. 5 is a $^1$H NMR spectrum of the secondary crystallization sample in Example 2.

In the accompanying drawings, FIG. 1 is a liquid chromatogram of a semi-synthetic concentrated crude product in Example 2 of the present disclosure; FIG. 2 is a liquid chromatogram of a semi-synthetic concentrated crude product in Comparative Example 1 of the present disclosure; FIG. 3 is a liquid chromatogram of a primary crystallization substance in Example 2; FIG. 4 is a liquid chromatogram of a secondary crystallization substance in Example 2; and FIG. 5 is a $^1$H NMR spectrum of a secondary crystallization product in Example 2.

Analytical results of elements of the secondary crystallization substance of Example 2 in Table 6 are as shown in Table 7:

TABLE 7

| Element | C | H | O |
|---|---|---|---|
| Theoretical value | 59.21% | 3.98% | 36.81% |
| Analytical value | 59.20% | 3.98% | 36.82% |

Conclusion: An error range of ratio of the analytical value to the theoretical value in Table 7 meets requirements (<±0.3%)

The ¹H NMR characterization data of the semi-synthetic dihydroquercetin (derived from the secondary crystallization sample in Example 2) in the present disclosure are as follows:

Formula (II)

¹H NMR (400 Hz, DMSO-d6) δ 11.90 (s, 1H), 10.85 (b, 1H), 9.06-9.01 (m, 2H), 6.88 (s, 1 H), 6.74 (s, 2H), 5.91 (d, J=1.9 Hz, 1 H), 5.86 (d, J=1.9 Hz, 1H), 5.77 (d, J=6.1 Hz, 1H), 4.98 (d, J=11.2 Hz, 1H), 4.50 (dd, J=11.2, 5.9 Hz, 1H).

Analysis of ¹H NMR characterization data is as follows.

As can be seen from the ¹H NMR spectrum shown above, hydrogen at sites 2, 3 of this compound is trans (1:1 mixture of two isomers 2R, 3R and 2S, 3S), because a coupling constant of the two H is 11.2 Hz. If the two H are cis, the coupling constant should be 2-3 Hz.

As can be seen from the ¹H NMR spectrum shown above, there is extremely few cis isomer content in the sample, the signal at δ 5.34 is H-2 signal of cis isomer, which is extremely weak, and the integral is <0.01. The integral of the H-2 signal of trans isomer is 1, thus the proportion of the cis isomer is <1.0%, then the proportion of the trans isomer is >99.0%.

Conclusion: The proportion of the trans isomers in the sample for test is up to 99% or more, which is consistent with the trans configuration of natural dihydroquercetin.

Notes: The ¹H NMR spectrum and analytical result of the above sample for test are derived from the Department of Chemistry, University of Science and Technology of China.

The above-mentioned are merely for preferred embodiments of the present disclosure, and are not intended to limit the present disclosure. For those skilled in the art, various modifications and variations could be made to the present disclosure. Any modifications, equivalent substitutions, improvements and the like made within the spirit and principle of the present disclosure should be covered within the scope of protection of the present disclosure.

INDUSTRIAL APPLICABILITY

The present disclosure provides a semi-synthetic method of dihydroquercetin. This method has significant advantages of short reaction steps, inexpensive and harmless reaction solvent, inexpensive reducing agent that is safe to store and transport, simple purification process of crude product, fewer pollutants, and low production costs. Moreover, the unreacted low-purity starting raw material (filter cake) can be fully recycled for reuse after simple and efficient purification treatment, which can further reduce the cost of the semi-synthetic raw material. In particular, the trans isomer of the target product obtained by the present semi-synthetic method account for 99% or higher, which is consistent with the trans configuration of natural quercetin. Therefore, it has very good promotion and application value, and is particularly suitable for large-scale industrial production.

What is claimed is:

1. A preparation method of dihydroquercetin, comprising the steps of:
    adding quercetin dihydrate to a reaction solvent of water adjusted to be alkaline with an alkalizing reagent, heating and stirring to dissolve the quercetin dihydrate, and then adding thiourea dioxide under protection of an inert gas to perform a reduction reaction, to obtain an endpoint reduction reaction solution;
    diluting the endpoint reduction reaction solution with water and cooling a resultant, and then acidizing, aging, and filtering the resultant to obtain a filtrate and a filter cake; and
    extracting, washing, drying, and concentrating the filtrate to obtain a concentrated crude product, and repeatedly crystallizing the concentrated crude product to obtain the dihydroquercetin.

2. The preparation method of dihydroquercetin according to claim 1, wherein a mass ratio of the quercetin dihydrate to the reaction solvent of water is 1:140-200.

3. The preparation method of dihydroquercetin according to claim 2, wherein the mass ratio of the quercetin dihydrate to the reaction solvent of water is 1:160-180.

4. The preparation method of dihydroquercetin according to claim 1, wherein the alkalizing reagent is at least one selected from the group consisting of sodium carbonate, potassium carbonate, and calcium carbonate.

5. The preparation method of dihydroquercetin according to claim 4, wherein the alkalizing reagent is at least one selected from the group consisting of sodium carbonate and potassium carbonate.

6. The preparation method of dihydroquercetin according to claim 1, wherein a molar ratio of the quercetin dihydrate to the alkalizing reagent is 1:3.5-6.5.

7. The preparation method of dihydroquercetin according to claim 1, wherein a molar ratio of the quercetin dihydrate to the thiourea dioxide is 1:2.5-7.5.

8. The preparation method of dihydroquercetin according to claim 1, wherein a reaction temperature of the reduction reaction is 60-100° C.

9. The preparation method of dihydroquercetin according to claim 1, wherein a reaction time of the reduction reaction is 60-120 min.

10. The preparation method of dihydroquercetin according to claim 1, wherein the acidizing process refers to acidification of the resultant with a dilute acid.

11. The preparation method of dihydroquercetin according to claim 10, wherein a pH value of an acidification endpoint is 0.5-3.5 for the concentrated crude product.

12. The preparation method of dihydroquercetin according to claim 1, wherein an extraction solvent is used in the extracting step, wherein the extraction solvent is a hydrophobic organic solvent.

13. The preparation method of dihydroquercetin according to claim 1, wherein the process of repeated crystallization comprises: subjecting the concentrated crude product to primary crystallization to obtain a primary crystallization product; and crystallizing the primary crystallization product to obtain a secondary crystallization product.

14. The preparation method of dihydroquercetin according to claim 13, wherein a concentration of a lower aliphatic alcohol contained in an alcohol-water mixed solvent for the repeated crystallization is 20%-80 v/v %.

15. The preparation method of dihydroquercetin according to claim 13, wherein in the primary crystallization, a material-liquid ratio of the concentrated crude product to a solvent for the repeated crystallization is 1:3.0-10.0.

16. The preparation method of dihydroquercetin according to claim 13, wherein in the secondary crystallization, a material-liquid ratio of the primary crystallization product to a solvent for the repeated crystallization is 1:3.5-9.5.

17. The preparation method of dihydroquercetin according to claim 1, wherein the filter cake is recycled after being washed with a dilute alcohol solution.

18. The preparation method of dihydroquercetin according to claim 17, wherein a concentration of alcohol in the dilute alcohol solution is 10%-80 v/v %.

19. The preparation method of dihydroquercetin according to claim 17, wherein the washing lasts for 10-30 min.

20. The preparation method of dihydroquercetin according to claim 17, wherein a temperature of the washing is room temperature to 60° C.

* * * * *